United States Patent
Takafuji et al.

(10) Patent No.: US 9,611,367 B2
(45) Date of Patent: *Apr. 4, 2017

(54) FILM

(71) Applicant: KURARAY CO., LTD., Kurashiki-shi (JP)

(72) Inventors: Masahiro Takafuji, Kurashiki (JP); Takanori Isozaki, Kurashiki (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/910,952

(22) PCT Filed: Aug. 5, 2014

(86) PCT No.: PCT/JP2014/070604
§ 371 (c)(1),
(2) Date: Feb. 8, 2016

(87) PCT Pub. No.: WO2015/020045
PCT Pub. Date: Feb. 12, 2015

(65) Prior Publication Data
US 2016/0194465 A1 Jul. 7, 2016

(30) Foreign Application Priority Data
Aug. 9, 2013 (JP) ................. 2013-165994

(51) Int. Cl.
| | | |
|---|---|---|
| C08J 5/18 | (2006.01) |
| C08F 8/12 | (2006.01) |
| B44C 1/175 | (2006.01) |
| C08F 216/06 | (2006.01) |
| C08F 218/08 | (2006.01) |
| A01N 25/00 | (2006.01) |
| B41F 16/00 | (2006.01) |

(52) U.S. Cl.
CPC .............. C08J 5/18 (2013.01); A01N 25/00 (2013.01); B41F 16/00 (2013.01); B44C 1/1758 (2013.01); C08F 8/12 (2013.01); C08F 216/06 (2013.01); C08F 218/08 (2013.01); C08J 2329/04 (2013.01)

(58) Field of Classification Search
None
See application file for complete search history.

(56) References Cited

U.S. PATENT DOCUMENTS

| | | | |
|---|---|---|---|
| 3,926,635 A | 12/1975 | Saleck et al. | |
| 2002/0022090 A1* | 2/2002 | Cho | B41M 5/025 427/282 |
| 2015/0210788 A1* | 7/2015 | Okamoto | B32B 27/306 428/36.92 |

FOREIGN PATENT DOCUMENTS

| | | |
|---|---|---|
| GB | 1 356 189 A | 6/1974 |
| JP | 50-038527 A | 4/1975 |
| JP | 53-099334 A | 8/1978 |
| JP | 04-164998 A | 6/1992 |
| JP | 07-506857 A | 7/1995 |
| JP | 11-198304 A | 7/1999 |
| JP | 2002-284818 A | 10/2002 |
| JP | 2005-060636 A | 3/2005 |
| JP | 2013-177576 A | 9/2013 |
| JP | 2014-034647 A | 2/2014 |
| WO | WO 2014/024912 * 2/2014 ............ C08F 216/04 |

OTHER PUBLICATIONS

International Search Report issued on Nov. 11, 2014 for PCT/JP2014/070604 filed on Aug. 5, 2014.

* cited by examiner

*Primary Examiner* — Brian Gulledge
(74) *Attorney, Agent, or Firm* — Oblon, McClelland, Maier & Neustadt, L.L.P.

(57) ABSTRACT

[Problem] To provide a film that has excellent water solubility which changes little over time even when the film touches a chemical, a package and a liquid transfer printing film each using the film and a liquid transfer printing method using the liquid transfer printing film.
[Means for Resolution] A film containing a hydroxymethyl group-containing vinyl alcohol-based polymer containing a vinyl alcohol unit and a unit structure represented by the following formula (1), a package and a liquid transfer printing film each using the film and a liquid transfer printing method using the liquid transfer printing film.

[Chem. 1]

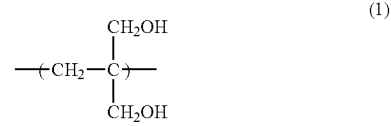

(1)

10 Claims, No Drawings

FILM

TECHNICAL FIELD

The present invention relates to a film containing a hydroxymethyl group-containing vinyl alcohol-based polymer having a 1,3-diol structure, a package and a liquid transfer printing film each using the film and a liquid transfer printing method using the liquid transfer printing film.

BACKGROUND ART

A vinyl alcohol-based polymer (sometimes referred to as "PVA" below) is one of a few crystalline water-soluble polymers. Using the excellent water solubility and the film properties (strength, oil resistance, film formability, oxygen gas barrier property and the like), a PVA is widely used for emulsifiers, suspending agents, surfactants, fiber-processing agents, various binders, paper-processing agents, adhesives, films and the like. Regarding films of the uses, some applications for water-soluble films making use of the excellent water solubility are known.

In an example method, a unit amount of a chemical or the like such as an agricultural chemical and a detergent is sealed and packaged in a film (unit packaging), and when the content is used, the package is directly put into water and the content is dissolved or dispersed in water together with the packaging film. Advantages of the unit packaging are that hazardous chemicals can be used without directly touching the chemicals, that the measurement of the amount to be used is not necessary because a certain amount is packaged and that post-treatment of the packaging container, the bag or the like is not necessary or easy, for example.

In addition to the unit packaging, a method of using a liquid transfer printing film obtained by forming a print layer to be transferred on a surface of a water-soluble or water-expansive film such as a PVA film is known as means for forming a print layer on the surface of a molded item with an uneven three-dimensional surface or a curved surface to print a design or improve the surface properties. For example, PTL 1 describes a method for transferring a print layer to a surface of an object to be printed using liquid pressure by floating a liquid transfer printing film on the surface of a liquid, which is typically water, with the printed surface facing upwards and then pushing a molded item, which is the object to be printed, into the film from above.

CITATION LIST

Patent Literature

PTL 1: JP-A-54-33115

SUMMARY OF INVENTION

Technical Problem

A film using an unmodified partially saponified PVA has been used as a film for the unit packaging. This film dissolves easily in cold water and has good properties. However, the film gradually reacts with the chemical, auxiliary agents (an activator, a dispersing agent or a carrier) which are used for processing the chemical or the like. As a result, the water solubility of the film deteriorates over time, and the film does not dissolve in water or hardly dissolves in water after long-term storage. Also, in many cases, the package cannot be used because of the leakage of the chemical. These points have been considered to be problems. A film using an unmodified partially saponified PVA has also been used as a base film for liquid transfer printing (a water-soluble or water-expansive film) used for producing a liquid transfer printing film. However, the water solubility of the film sometimes changes over time due to the environment in which the film is stored or by the influence of the ink components used for printing or of the chemicals such as an ink activator used for liquid transfer printing.

An object of the invention is to provide a film that has excellent water solubility which changes little over time even when the film touches a chemical, a package and a liquid transfer printing film each using the film and a liquid transfer printing method using the liquid transfer printing film.

Solution to Problem

The present inventors have made intensive investigations to achieve the object and, as a result, found that the problems are solved by a film containing a hydroxymethyl group-containing PVA containing a specific structural unit having a 1,3-diol structure in the main chain. The inventors have made further investigations based on the findings and completed the invention.

That is, the invention relates to:

[1] a film containing a hydroxymethyl group-containing PVA containing a vinyl alcohol unit and a structural unit represented by the following formula (1);

[Chem. 1]

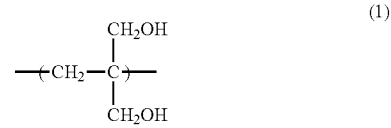

[2] the film according to [1], wherein the proportion of the structural unit represented by the formula (1) in the hydroxymethyl group-containing PVA is 0.1 to 30 mol %;
[3] the film according to [1], wherein the proportion of the structural unit represented by the formula (1) in the hydroxymethyl group-containing PVA is 2 to 10 mol %;
[4] the film according to any one of [1] to [3], wherein the saponification degree of the hydroxymethyl group-containing PVA is 95 to 99.9 mol %;
[5] the film according to any one of [1] to [4] which is a chemical packaging film;
[6] the film according to anyone of [1] to [4] which is abase film for liquid transfer printing;
[7] a package comprising a chemical packaged in the film according to [5];
[8] the package according to [7], wherein the chemical is an agricultural chemical or a detergent;
[9] a liquid transfer printing film obtained by printing on a surface of the film according to [6]; and
[10] a liquid transfer printing method having a step of floating the liquid transfer printing film according to [9] on the surface of a liquid with the printed surface facing upwards and a step of pushing an object to be printed into the floating liquid transfer printing film from above.

Advantageous Effects of Invention

According to the invention, a film that has excellent water solubility which changes little overtime even when the film touches a chemical, a package and a liquid transfer printing film each using the film and a liquid transfer printing method using the liquid transfer printing film are provided.

DESCRIPTION OF EMBODIMENTS

The film of the invention contains a hydroxymethyl group-containing PVA containing a vinyl alcohol unit and a structural unit represented by the following formula (1).

[Chem. 2]

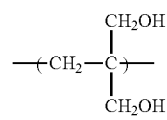

(1)

The film of the invention has improved water solubility and improved stability of the water solubility when the film touches a chemical, because the hydroxymethyl group-containing PVA contained in the film contains a structural unit which is represented by the formula (1) and which has a 1,3-diol structure. Although the invention is not limited at all, one of the possible reasons why the advantages can be obtained is that the structural unit represented by the formula (1) decreases the crystallinity.

The proportion of the structural unit represented by the formula (1) in the hydroxymethyl group-containing PVA is not particularly limited, but the proportion based on the number of moles (100 mol %) of all the structural units composing the hydroxymethyl group-containing PVA is preferably in the range of 0.1 to 30 mol %, more preferably in the range of 1 to 20 mol %, and particularly preferably in the range of 2 to 10 mol %. When the proportion is 0.1 mol % or more, the water solubility of the film and the stability of the water solubility when the film touches a chemical further improve. On the other hand, when the proportion is 30 mol % or less, the toughness of the film can be effectively prevented from deteriorating due to the excessive decrease in the crystallinity of the film. In this description, a structural unit means a repeating unit composing the polymer.

The polymerization degree of the hydroxymethyl group-containing PVA is not particularly limited but is preferably in the range of 100 to 7,000, more preferably in the range of 200 to 5,000, and further preferably in the range of 200 to 4,000. When the polymerization degree is 100 or more, the strength of the film improves. On the other hand, when the polymerization degree is 7,000 or less, the industrial production of the hydroxymethyl group-containing PVA becomes easy. In this description, the polymerization degree of the hydroxymethyl group-containing PVA means the average polymerization degree measured in accordance with the description of JIS K6726-1994.

The saponification degree of the hydroxymethyl group-containing PVA is not particularly limited. However, the saponification degree is preferably in the range of 80 to 99.99 mol % from the viewpoint of further improvement of the water solubility and also because the production of a hydroxymethyl group-containing PVA having an excessively high saponification degree is difficult, and the saponification degree is preferably in the range of 95 to 99.9 mol % especially because the stability of the water solubility when the film touches a chemical further improves. In this description, the saponification degree of the hydroxymethyl group-containing PVA means the proportion of the number of moles (mol %) of the vinyl alcohol unit ($-CH_2-CH(OH)-$) in the total number of moles of a structural unit which can be converted to a vinyl alcohol unit by saponification (typically a vinyl ester unit) and the vinyl alcohol unit contained in the hydroxymethyl group-containing PVA. The saponification degree can be measured in accordance with the description of JIS K6726-1994 also considering the amounts of the structural unit represented by the formula (1) and a derivative thereof.

The method for producing the hydroxymethyl group-containing PVA is not particularly limited. In an example method, a vinyl ester monomer and an unsaturated monomer which can be copolymerized with the vinyl ester monomer and which can be converted to the structural unit represented by the formula (1) are copolymerized, and the vinyl ester unit of the obtained vinyl ester-based copolymer is converted to a vinyl alcohol unit while the structural unit derived from the unsaturated monomer which can be converted to the structural unit represented by the formula (1) is converted to the structural unit represented by the formula (1). A specific example of the unsaturated monomer which can be converted to the structural unit represented by the formula (1) is shown by the following formula (2).

[Chem. 3]

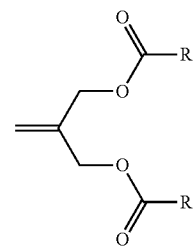

(2)

In the formula (2), R represents an alkyl group having 1 to 10 carbon atoms. The structure of R is not particularly limited and may have a branch or a cyclic structure in a part thereof. Also, a part of R may be substituted with another functional group. R is preferably an alkyl group having 1 to 5 carbon atoms, and examples of the alkyl group are linear or branched alkyl groups such as methyl group, ethyl group, n-propyl group, isopropyl group, n-butyl group, isobutyl group, tert-butyl group and pentyl group. The substituents that R may have are alkoxy groups, halogen atoms, hydroxyl group and the like. Rs may be the same or different from each other.

The unsaturated monomer represented by the formula (2) is for example 1,3-diacetoxy-2-methylenepropane, 1,3-dipropionyloxy-2-methylenepropane, 1,3-dibutyryloxy-2-methylenepropane or the like. Of these examples, 1,3-diacetoxy-2-methylenepropane is preferably used in view of the easiness of production.

The copolymerization reaction of a vinyl ester monomer with the unsaturated monomer represented by the formula (2) progresses easier than the copolymerization reaction with other allyl unsaturated monomers (for example, allyl glycidyl ether or the like) which are generally used for modifying a PVA. Thus, there are only a few restrictions on the modification degree and the polymerization degree during the polymerization, and a hydroxymethyl group-containing PVA having a high modification degree and a high polymerization degree is obtained easily. Also, because the amount of the unreacted unsaturated monomer that remains when the polymerization finishes can be reduced, the hydroxymethyl group-containing PVA of the invention is excellent also in terms of the environmental issues and the costs of the industrial production.

The vinyl ester monomer used for producing the hydroxymethyl group-containing PVA is not particularly limited but is for example vinyl formate, vinyl acetate, vinyl propionate, vinyl butyrate, vinyl isobutyrate, vinyl pivalate, vinyl versatate, vinyl caproate, vinyl caprylate, vinyl caprate, vinyl laurate, vinyl palmitate, vinyl stearate, vinyl oleate, vinyl benzoate or the like. From an economical viewpoint, vinyl acetate is preferable.

The polymerization style for copolymerizing the unsaturated monomer represented by the formula (2) and the vinyl ester monomer may be any of batch polymerization, semi-batch polymerization, continuous polymerization, semi-continuous polymerization and the like. As the polymerization method, a known method such as a bulk polymerization method, a solution polymerization method, a suspension polymerization method and an emulsion polymerization method can be applied. A bulk polymerization method or a solution polymerization method in which the polymerization progresses without any solvent or in a solvent such as an alcohol is generally used. When a vinyl ester-based copolymer having a high polymerization degree is to be obtained, an emulsion polymerization method is also preferable. The solvent used for the solution polymerization method is not particularly limited but is for example an alcohol. The alcohol used as the solvent for the solution polymerization method is for example a lower alcohol such as methanol, ethanol and propanol. The amount of the solvent used in the polymerization system may be determined considering the chain transfer of the solvent depending on the polymerization degree of the hydroxymethyl group-containing PVA to be obtained. When the solvent is methanol for example, the ratio of the mass of the solvent to the mass of all the monomers contained in the polymerization system {=(solvent)/(all the monomers)} is determined preferably in the range of 0.01 to 10, and more preferably in the range of 0.05 to 3.

The polymerization initiator used for the copolymerization of the unsaturated monomer represented by the formula (2) and the vinyl ester monomer may be selected from known polymerization initiators such as azo initiators, peroxide initiators and redox initiators depending on the polymerization method. The azo initiators are for example 2,2'-azobisisobutyronitrile, 2,2'-azobis(2,4-dimethylvaleronitrile) and 2,2'-azobis(4-methoxy-2,4-dimethylvaleronitrile). The peroxide initiators are for example percarbonate compounds such as diisopropyl peroxydicarbonate, di-2-ethylhexyl peroxydicarbonate and diethoxyethyl peroxydicarbonate; perester compounds such as t-butyl peroxyneodecanoate and α-cumyl peroxyneodecanoate; acetyl cyclohexyl sulfonyl peroxide; 2,4,4-trimethylpentyl-2-peroxyphenoxyacetate; and acetyl peroxide. The polymerization initiator may be a combination of potassium persulfate, ammonium persulfate, hydrogen peroxide or the like with any of the initiators. The redox initiators are for example polymerization initiators obtained by combining any of the peroxide initiators with a reducing agent such as sodium hydrogen sulfite, sodium hydrogen carbonate, tartaric acid, L-ascorbic acid and Rongalite. The amount of the polymerization initiator to be used varies with the kind of polymerization initiator and thus cannot be determined generally, but the amount may be determined depending on the polymerization rate. For example, when 2,2'-azobisisobutyronitrile or acetyl peroxide is used as the polymerization initiator, the amount based on the vinyl ester monomer is preferably 0.01 to 0.2 mol %, and more preferably 0.02 to 0.15 mol %. The polymerization temperature is not particularly limited. However, a temperature from room temperature to about 150° C. is suitable, and the polymerization temperature is preferably 40° C. or higher and the boiling temperature of the solvent used or lower.

The unsaturated monomer represented by the formula (2) and the vinyl ester monomer may be copolymerized in the presence of a chain transfer agent. The chain transfer agent is for example an aldehyde such as acetaldehyde and propionaldehyde; a ketone such as acetone and methyl ethyl ketone; a mercaptan such as 2-hydroxyethanethiol; a phosphinate such as sodium phosphinate monohydrate; or the like. Of the examples, an aldehyde and a ketone are preferably used. The amount of the chain transfer agent to be used can be determined according to the chain transfer coefficient of the chain transfer agent used and the polymerization degree of the hydroxymethyl group-containing PVA to be obtained but, in general, is preferably 0.1 to 10 parts by mass based on 100 parts by mass of the vinyl ester monomer.

The hydroxymethyl group-containing PVA can be obtained by saponifying the vinyl ester-based copolymer obtained by the copolymerization of the unsaturated monomer represented by the formula (2) and the vinyl ester monomer. By saponifying the vinyl ester-based copolymer, the vinyl ester unit of the vinyl ester-based copolymer is converted to a vinyl alcohol unit. Also, the ester bond in the structural unit derived from the unsaturated monomer represented by the formula (2) is saponified, and the structural unit is converted to the structural unit which is represented by the formula (1) and which has a 1,3-diol structure. Therefore, the hydroxymethyl group-containing PVA can be produced without any further reaction such as hydrolysis after the saponification.

The saponification of the vinyl ester-based copolymer can be conducted for example using the vinyl ester-based copolymer dissolved in an alcohol or a hydrous alcohol. The alcohol used for the saponification is for example a lower alcohol such as methanol and ethanol and is preferably methanol. The alcohol used for the saponification may contain another solvent such as acetone, methyl acetate, ethyl acetate or benzene for example in the proportion of 40 mass % or less of the mass of the alcohol. The catalyst used for the saponification is for example an alkali metal hydroxide such as potassium hydroxide and sodium hydroxide, an alkali catalyst such as sodium methylate or an acid catalyst such as a mineral acid. The temperature of the saponification is not limited but is preferably in the range of 20 to 60° C. When a gel product precipitates as the saponification progresses, the hydroxymethyl group-containing PVA can be obtained by pulverizing the product and then washing and drying the product. As the saponification method, not only the method described above but also known methods can be applied.

The hydroxymethyl group-containing PVA can further contain a structural unit other than the structural unit represented by the formula (1), the vinyl alcohol unit and the vinyl ester unit. The other structural unit is for example a structural unit derived from an ethylenic unsaturated monomer which can be copolymerized with the vinyl ester monomer. Also, a structural unit derived from the unsaturated monomer which can be copolymerized with the vinyl ester monomer and which can be converted to the structural unit represented by the formula (1) (the structural unit which has not been converted to the structural unit represented by the formula (1) through the saponification) can be contained.

The total proportion of the structural unit represented by the formula (1), the vinyl alcohol unit and the vinyl ester unit in the hydroxymethyl group-containing PVA, based on the number of moles (100 mol %) of all the structural units composing the hydroxymethyl group-containing PVA, is preferably 80 mol % or more, more preferably 90 mol % or more, and further preferably 95 mol % or more. The total proportion may be 99 mol % or more.

The ethylenic unsaturated monomer is for example an α-olefin such as ethylene, propylene, n-butene, isobutylene and 1-hexene; acrylic acid or a salt thereof; an unsaturated monomer having an acrylic acid ester group; methacrylic acid or a salt thereof; an unsaturated monomer having a methacrylic acid ester group; acrylamide; an acrylamide derivative such as N-methylacrylamide, N-ethylacrylamide, N,N-dimethylacrylamide, diacetone acrylamide, acrylamide propanesulfonic acid and a salt thereof and acrylamide propyldimethylamine and a salt thereof (for example a quaternary salt); methacrylamide; a methacrylamide derivative such as N-methylmethacrylamide, N-ethylmethacrylamide, methacrylamide propanesulfonic acid and a salt thereof and methacrylamide propyldimethylamine and a salt thereof (for example a quaternary salt); a vinyl ether such as methyl vinyl ether, ethyl vinyl ether, n-propyl vinyl ether, i-propyl vinyl ether, n-butyl vinyl ether, i-butyl vinyl ether, t-butyl vinyl ether, dodecyl vinyl ether, stearyl vinyl ether and 2,3-diacetoxy-1-vinyloxy propane; a vinyl cyanide such as acrylonitrile and methacrylonitrile; a vinyl halide such as vinyl chloride and vinyl fluoride; a vinylidene halide such as vinylidene chloride and vinylidene fluoride; an allyl compound such as allyl acetate, 2,3-diacetoxy-1-allyloxypropane and allyl chloride; an unsaturated dicarboxylic acid such as maleic acid, itaconic acid and fumaric acid, a salt thereof or an ester thereof; a vinylsilyl compound such as vinyltrimethoxysilane; or isopropenyl acetate.

The order of alignment of the structural unit represented by the formula (1), the vinyl alcohol unit and the other optional structural units in the hydroxymethyl group-containing PVA is not particularly limited and may be any of random, block and alternating structures and the like.

The film of the invention can contain a plasticizer in addition to the hydroxymethyl group-containing PVA. A preferable plasticizer is a polyhydric alcohol. Specific examples include ethylene glycol, glycerin, propylene glycol, diethylene glycol, diglycerin, triethylene glycol, tetraethylene glycol, trimethylolpropane and the like. The film of the invention can contain a kind or two or more kinds of the plasticizers. Of these examples, glycerin is preferable.

The plasticizer content of the film of the invention based on 100 parts by mass of the hydroxymethyl group-containing PVA contained in the film is preferably 50 parts by mass or less, more preferably 45 parts by mass or less, and further preferably 40 parts by mass or less. When the content is 50 parts by mass or less, the film can be inhibited from becoming too flexible and the handleability can be inhibited from deteriorating.

For the purposes of giving mechanical strength, maintaining the moisture resistance during the handling of the film or regulating the speed of softening by water absorption during the dissolution of the film or the period required for the diffusion in water, for example, the film of the invention may contain starch and/or a water-soluble polymer other than the hydroxymethyl group-containing PVA described above.

The starch is for example natural starch such as corn starch, potato starch, sweet potato starch, wheat starch, rice starch, tapioca starch and sago starch; processed starch such as esterified starch, esterified starch and oxidized starch; or the like, and processed starch is particularly preferable.

The starch content of the film of the invention based on 100 parts by mass of the hydroxymethyl group-containing PVA contained in the film is preferably 15 parts by mass or less, and more preferably 10 parts by mass or less. When the content is 15 parts by mass or less, the impact resistance of the film improves, and the property of passing through the processes improves.

The water-soluble polymer other than the hydroxymethyl group-containing PVA is for example dextrin, gelatin, glue, casein, shellac, gum arabic, polyacrylic acid amide, sodium polyacrylate, polyvinyl methyl ether, a copolymer of methyl vinyl ether and maleic anhydride, a copolymer of vinyl acetate and itaconic acid, polyvinylpyrrolidone, cellulose, acetyl cellulose, acetyl butyl cellulose, carboxymethyl cellulose, methyl cellulose, ethyl cellulose, hydroxyethyl cellulose, sodium alginate or the like.

The content of the water-soluble polymer other than the hydroxymethyl group-containing PVA in the film of the invention based on 100 parts by mass of the hydroxymethyl group-containing PVA contained in the film is preferably 15 parts by mass or less, and more preferably 10 parts by mass or less. When the content is 15 parts by mass or less, the water solubility and the dispersibility of the film improve.

The film of the invention can further suitably contain an additive such as a filler, a processing stabilizer (a copper compound or the like), a weather resistance stabilizer, a colorant, an ultraviolet absorber, a light stabilizer, an antioxidant, an antistatic agent, a flame retardant, another thermoplastic resin, a lubricant, fragrance, a defoaming agent, a deodorant, an extender, a remover, a release agent, a reinforcing agent, a crosslinking agent, a fungicide, an antiseptic agent and an agent for decreasing the crystallization rate, according to need.

The total proportion of the hydroxymethyl group-containing PVA, the plasticizer, the starch and the water-soluble polymer other than the hydroxymethyl group-containing PVA in the film of the invention based on the mass of the film is preferably 80 mass % or more, more preferably 90 mass % or more, and further preferably 95 mass % or more.

The thickness of the film of the invention is not particularly limited. However, from the viewpoint of balance between the strength and the water solubility, the thickness is generally 1 to 100 μm, further preferably 5 to 75 μm, and particularly preferably about 10 to 60 μm.

The length and the width of the film of the invention are not particularly limited. From the viewpoint of the productivity during processing, the length is preferably 1 m or more, more preferably 100 m or more, and further preferably 1,000 m or more, and the width is preferably 50 cm or more, more preferably 80 cm or more, and further preferably 100 cm or more.

The method for producing the film of the invention is not particularly limited, and a production method by which the thickness and the width of the formed film become more even can be preferably used. For example, the film can be produced using a raw film-formation solution obtained by dissolving the hydroxymethyl group-containing PVA composing the film and, according to need, a kind or two or more kinds of the plasticizer, the starch, the other water-soluble polymer, the additive, the surfactant described below and the like in a liquid medium or using a raw film-formation solution which contains the hydroxymethyl group-containing PVA and, according to need, a kind or two or more kinds of the plasticizer, the starch, the other water-soluble polymer, the additive, the surfactant, a liquid medium and the like and in which the hydroxymethyl group-containing PVA is melted. When the raw film-formation solution contains at least a kind of the plasticizer, the starch, the other water-soluble polymer, the additive and the surfactant, these components are preferably mixed uniformly.

The liquid medium used for preparing the raw film-formation solution is for example water, dimethyl sulfoxide, dimethylformamide, dimethylacetamide, N-methylpyrrolidone, ethylene glycol, glycerin, propylene glycol, diethylene glycol, triethylene glycol, tetraethylene glycol, trimethylolpropane, ethylenediamine, diethylenetriamine or the like, and a kind or two or more kinds thereof can be used. Of these examples, water is preferable in view of the environmental burden and the recovery.

The volatile component content of the raw film-formation solution (the proportion of the volatile components which are removed through volatilization or evaporation during the film formation, such as the liquid medium, in the raw film-formation solution) varies with the film formation method, the conditions of the film formation and the like, but in general, the volatile component content is preferably in the range of 50 to 95 mass %, more preferably in the range of 55 to 90 mass %, and further preferably in the range of 60 to 85 mass %. When the volatile component content of the raw film-formation solution is 50 mass % or more, the viscosity of the raw film-formation solution does not become too high, and filtration and defoaming during the preparation of the raw film-formation solution are conducted smoothly. Also, a film with a few foreign matters and a few defects is easily produced. On the other hand, when the volatile component content of the raw film-formation solution is 95 mass % or less, the concentration of the raw film-formation solution does not become too low, and the industrial production of the film becomes easy.

The raw film-formation solution preferably contains a surfactant. When a surfactant is contained, the film formability improves, and the unevenness of the film thickness is inhibited from being generated. Also, the removal of the film from a metal roll or a belt used for the film formation becomes easy. When the film is produced using a raw film-formation solution containing a surfactant, the film may contain the surfactant. The kind of the surfactant is not particularly limited, but from the viewpoint of the removability from a metal roll or a belt or the like, an anionic surfactant or a nonionic surfactant is preferable.

As the anionic surfactant, for example, carboxylic acid type such as potassium laurate; sulfuric acid ester type such as polyoxyethylene lauryl ether sulfates and octyl sulfates; sulfonic acid type such as dodecylbenzenesulfonates; and the like are preferable.

As the nonionic surfactant, for example, alkyl ether type such as polyoxyethylene oleyl ether; alkylphenyl ether type such as polyoxyethylene octylphenyl ether; alkyl ester type such as polyoxyethylene laurate; alkyl amine type such as polyoxyethylene lauryl amino ether; alkyl amide type such as polyoxyethylene lauric acid amide; polypropylene glycol ether type such as polyoxyethylene polyoxypropylene ether; alkanolamide type such as lauric acid diethanolamide and oleic acid diethanolamide; allyl phenyl ether type such as polyoxyalkylene allyl phenyl ether; and the like are preferable.

A kind of the surfactants can be used alone, or a combination of two or more kinds thereof can be used.

When the raw film-formation solution contains a surfactant, the surfactant content based on 100 parts by mass of the hydroxymethyl group-containing PVA contained in the raw film-formation solution is preferably in the range of 0.01 to 5 parts by mass, more preferably in the range of 0.02 to 4 parts by mass, and particularly preferably in the range of 0.05 to 3 parts by mass. When the content is 0.01 parts by mass or more, the film formability and the removability further improve. On the other hand, when the content is 5 parts by mass or less, it is possible to inhibit the deterioration of the handleability due to blocking caused when the surfactant bleeds out on the surface of the film.

When the film is formed using the raw film-formation solution described above, the film formation method is for example a cast film formation method, an extrusion film formation method, a wet film formation method, a gel film formation method or the like. Only one of these film formation methods may be used, or a combination of two or more thereof may be used. Of these film formation methods, a cast film formation method and an extrusion film formation method are preferable because a film having an even thickness and an even width and having good physical properties can be obtained. The formed film can be dried or heat treated according to need.

As an example of the specific method for producing the film of the invention, a method of evenly discharging or flow casting the raw film-formation solution on the outer surface of a first rotating heated roll (or belt) which is located at the most upstream part for example using a T-type slit die, a hopper plate, an I-die, a lip coater die or the like, drying the film by evaporating the volatile components from one of the surfaces of the film which has been discharged or flow cast on the outer surface of the first roll (or belt), subsequently further drying the film on the outer surface of one or more rotating heated rolls which are located at a downstream part or further drying the film by causing the film to pass through a hot-air drier and then rolling the film with a reeler can be industrially preferably used. Drying with heated rolls and drying with a hot-air drier may be suitably combined.

For the purpose of improving the slip property of the surface for example, the surface of the film of the invention is preferably matted. The matting method is an on-line matting method in which a mat surface of a roll or a belt is transferred to the film during the film formation, a method in which the formed film is once rolled into a roll and then embossed or the like. The arithmetic mean height (Ra) of the matted surface is preferably 0.5 µm or more, and more preferably 1 µm or more. The upper limit of the arithmetic mean height (Ra) is for example 10 µm. When the arithmetic mean height (Ra) is less than 0.5 µm, sufficient slip property is difficult to obtain. Also, the maximum height (Rz) is preferably 1 µm or more, and more preferably 3 µm or more. The upper limit of the maximum height (Rz) is for example 20 µm. When the maximum height (Rz) is less than 0.5 µm, sufficient slip property is difficult to obtain. In this description, the arithmetic mean height (Ra) and the maximum height (Rz) are those defined in JIS B 0601:2001.

Making use of the excellent water solubility and the stability of the water solubility when the film touches a chemical, the film of the invention can be preferably used for various water-soluble film applications. Such water-soluble films are for example a chemical packaging film, a base film for liquid transfer printing, an embroidery substrate film, a release film for forming artificial marble, a seed packaging film, a film for a dirt bag and the like. Of these examples, the film of the invention is preferably used as a chemical packaging film or a base film for liquid transfer printing because the effects of the invention are brought about more significantly.

When the film of the invention is used as a chemical packaging film, the kind of the chemical is an agricultural chemical, a detergent (including bleach) or the like. The physical properties of the chemical are not particularly limited, and the chemical may be an acidic, neutral or alkaline chemical. Also, the chemical may contain a boron-containing compound. The form of the chemical is powder or a mass or may be gel or liquid in some cases. The packaging form is not particularly limited, but the form of unit packaging in which a unit amount of the chemical is packaged (preferably sealed and packaged) is preferable. By packaging the chemical using the film of the invention as a chemical packaging film, the package of the invention is obtained.

When the film of the invention is used as a base film for liquid transfer printing, the liquid transfer printing film of the invention can be obtained by printing on a surface of the film of the invention. The printing method is not particularly limited, and a print layer can be formed using a known printing process. For example, gravure printing, screen printing, offset printing, roll coating or the like can be used. The film of the invention may be directly printed using a printing ink or can be also printed by once forming a print layer on another film and then transferring the print layer to the film of the invention. When the film of the invention is directly printed using a printing ink as in the former method, a restriction on the composition of the printing ink, a problem of the drying step, a problem of color shift in multicolor printing and the like sometimes arise. Thus, the film of the invention is preferably printed by once forming a print layer on another film and then transferring the print layer to the film of the invention as in the latter method. As the printing ink used for printing, conventionally known inks can be used.

Liquid transfer printing can be conducted by floating the liquid transfer printing film on the surface of a liquid such as water with the printed surface facing upwards and pushing an object to be printed such as a molded item into the film from above. A more detailed liquid transfer printing method is for example a liquid transfer printing method including a first step of floating the liquid transfer printing film on the surface of a liquid with the printed surface facing upwards and activating the print layer for example by spraying an ink activator, a second step of lowering and pushing an object to be printed with the surface to be printed facing downwards into the liquid transfer printing film floating on the liquid surface from above, a third step of sufficiently fixing the print layer of the liquid transfer printing film on the surface of the object to be printed and then removing the base film part for liquid transfer printing of the liquid transfer printing film and a fourth step of sufficiently drying the object to be printed after transferring the print layer to the surface to be printed.

The kind of the object to be printed is not particularly limited and is for example a wood substrate such as wood, plywood and a particle board; a plastic; a gypsum board; a fiber cement board such as a pulp cement board, a slate board and an asbestos cement board; a calcium silicate board; a magnesium silicate board; glass-fiber reinforced cement; concrete; a plate of a metal such as iron, stainless steel, copper and aluminum; a composite material thereof; or the like. The surface shape of the object to be printed may be flat, rough or uneven. However, an object to be printed with an uneven three-dimensional surface or a curved surface is preferable because the advantages of liquid transfer printing can be more effectively used.

EXAMPLES

The invention is explained in further detail below by Examples, but the invention is not limited by the Examples at all. The measurement and assessment methods used in the following Examples and Comparative Example are shown below.

Primary Structures of PVAs

The primary structures of the hydroxymethyl group-containing PVAs used in the following Examples were analyzed using 270 MHz $^1$H-NMR. As the solvent for the $^1$H-NMR measurement, deuterated DMSO was used.

Water Solubility of Films

A 1-L beaker containing 1 L of ion-exchanged water was put into a water bath controlled at 20° C., and a sample (size: 40 mm×40 mm) which was cut out of a film to be measured and which was fixed in a metal frame was put into the ion-exchanged water which was being stirred with a magnetic stirrer tip with a length of 30 mm made of Teflon (registered trademark) at a rotation rate of 300 rpm. The period required for the complete dissolution of the sample was measured and used as an indicator of the water solubility.

Stability of Water Solubility when Films Touched Chemical

A pair of bags of 10 cm×20 cm was made from each of the films produced in the Examples and the Comparative Example below, and 40 g of fine powder of an agricultural chemical (an insecticide, "Gamba" manufactured by Syngenta, wettable powder) was put into each of the bags. The bags were heat sealed. The agricultural chemical bags were further sealed with a film laminated with aluminum foil and polyethylene. As a hypothetical accelerated test for long-term storage, the agricultural chemical bags were left in an incubator at 40° C. One bag of each pair was taken out after a month, and the other one of each pair was taken out after three months. Samples were cut out of the film parts of the agricultural chemical bags, and the periods required for the complete dissolution of the samples were measured in a similar manner as in the assessment method described in "Water Solubility of Films" above. The periods were compared with the water solubility of the films (the periods required for the complete dissolution of the samples) before packaging the agricultural chemical, and the stability of the water solubility when the films touched a chemical was assessed.

Examples 1 to 4

An aqueous solution which contained 100 parts by mass of one of the hydroxymethyl group-containing PVAs shown in Table 1 obtained by saponifying a copolymer of vinyl acetate and 1,3-diacetoxy-2-methylenepropane, 20 parts by mass of glycerin as a plasticizer and 0.1 parts by mass of sodium polyoxyethylene lauryl ether sulfate as a surfactant and in which the proportion of the hydroxymethyl group-containing PVA was 10 mass % was used as a raw film-formation solution and dried on a metal roll at 80° C., and the film was removed from the metal roll and then heat treated at 100° C. for 10 minutes. In this manner, films having a thickness of 40 μm were produced.

Using the obtained films, the water solubility of the films and the stability of the water solubility when the films touched a chemical were assessed by the above methods. The results are shown in Table 1.

Comparative Example 1

A film having a thickness of 40 μm was produced in a similar manner as in Example 1 except that the unmodified PVA shown in Table 1 obtained by saponifying a homopolymer of vinyl acetate was used instead of the hydroxymethyl group-containing PVA of Example 1, and the measurement and the assessment were conducted. The results are shown in Table 1.

TABLE 1

| | PVA | | | Film | | | |
|---|---|---|---|---|---|---|---|
| | | | | Period required for complete dissolution of sample (film) | | | |
| | Polymerization degree | Saponification degree (Mol %) | Proportion of modified unit[1] (Mol %) | Before packaging agricultural chemical <<A>> (Second) | A month after packaging agricultural chemical (Second) | Three months after packaging agricultural chemical <<B>> (Second) | Change rate[2] (%) |
| Example 1 | 1,700 | 98.0 | 3.0 | 38 | 42 | 45 | 18 |
| Example 2 | 1,700 | 98.0 | 4.0 | 32 | 35 | 39 | 22 |
| Example 3 | 1,700 | 98.0 | 6.0 | 24 | 27 | 30 | 25 |
| Example 4 | 1,700 | 88.0 | 3.0 | 20 | 43 | 47 | 135 |
| Comparative Example 1 | 1,700 | 88.0 | — | 40 | >500 | >500 | >1000 |

[1] 1,3-dihydroxy-2-methylenepropane unit
[2] (100 × <<B>>/<<A>>) − 100

As it is obvious from the results above, it can be seen that the films of Examples 1 to 4, which satisfied the requirements of the invention, had excellent water solubility and that the water solubility of the films changed little over time even when the films touched a chemical.

The invention claimed is:

1. A film comprising a hydroxymethyl group-containing vinyl alcohol-based polymer comprising a vinyl alcohol unit and a structural unit of formula (1)

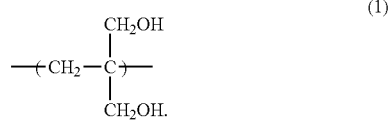

2. The film according to claim 1, wherein a proportion of the structural unit of formula (1) in the hydroxymethyl group-containing vinyl alcohol-based polymer is 0.1 to 30 mol %.

3. The film according to claim 1, wherein a proportion of the structural unit of formula (1) in the hydroxymethyl group-containing vinyl alcohol-based polymer is 2 to 10 mol %.

4. The film according to claim 1, wherein the saponification degree of the hydroxymethyl group-containing vinyl alcohol-based polymer is from 95 to 99.9 mol %.

5. The film according to claim 1, wherein the film is a chemical packaging film.

6. The film according to claim 1, wherein the film is a base film suitable for liquid transfer printing.

7. A package comprising a chemical packaged in the film according to claim 5.

8. The package according to claim 7, wherein the chemical is an agricultural chemical or a detergent.

9. A liquid transfer printing film obtained by printing on a surface of the film according to claim 6.

10. A liquid transfer printing method, comprising:
   floating the liquid transfer printing film according to claim 9 on a surface of a liquid with the printed surface facing upwards; and
   pushing an object to be printed into the floating liquid transfer printing film from above.

* * * * *